US011776687B2

(12) United States Patent
Ramachandran et al.

(10) Patent No.: US 11,776,687 B2
(45) Date of Patent: Oct. 3, 2023

(54) MEDICAL EXAMINATION OF HUMAN BODY USING HAPTICS

(71) Applicant: SONY GROUP CORPORATION, Tokyo (JP)

(72) Inventors: Ramu Ramachandran, Bangalore (IN); Sankar Shanmugam, Bangalore (IN); Abilash Rajarethinam, Bangalore (IN)

(73) Assignee: SONY GROUP CORPORATION, Tokyo (JP)

(*) Notice: Subject to any disclaimer, the term of this patent is extended or adjusted under 35 U.S.C. 154(b) by 70 days.

(21) Appl. No.: 17/094,564

(22) Filed: Nov. 10, 2020

(65) Prior Publication Data

US 2022/0148723 A1 May 12, 2022

(51) Int. Cl.
*G16H 40/67* (2018.01)
*G16H 50/50* (2018.01)
(Continued)

(52) U.S. Cl.
CPC .......... *G16H 40/67* (2018.01); *A61B 5/0064* (2013.01); *A61B 5/7267* (2013.01);
(Continued)

(58) Field of Classification Search
CPC .......... G06F 3/16; G06H 50/50; A61B 5/7445
See application file for complete search history.

(56) References Cited

U.S. PATENT DOCUMENTS 5,769,640 A * 6/1998 Jacobus ............... G09B 23/285
434/262
8,362,882 B2 1/2013 Heubel et al.
(Continued)

FOREIGN PATENT DOCUMENTS

CN 106200982 * 12/2016 ............. G16H 50/50
CN 111868788 A 10/2020
(Continued)

OTHER PUBLICATIONS

Gomez, et al., Development of a Virtual Reality Robotic Surgical Curriculum Using the Da Vinci Si Surgical System, Sages, Surgical Endoscopy, vol. 29, No. 8, Nov. 2014, pp. 2171-2179.
(Continued)

*Primary Examiner* — Matthew A Eason
*Assistant Examiner* — Scott Au
(74) *Attorney, Agent, or Firm* — CHIP LAW GROUP

(57) ABSTRACT

An electronic apparatus and method for medical examination of human body using haptics is provided. The electronic apparatus controls a first head-mounted display to render a 3D model of an anatomical portion of the body of a human subject. The rendered 3D model includes a region corresponding to defect portion in the anatomical portion. The electronic apparatus transmits a touch input to wearable sensor in contact with the anatomical portion. Such an input corresponds to a human touch on the region of the rendered 3D model. The electronic apparatus receives, based on the touch input, bio-signals associated with the defect portion via the wearable sensor. The bio-signals include physiological signals and somatic sensation information associated with the defect portion. As a response to the human touch, the electronic apparatus controls a wearable haptic device to generate a haptic feedback based on the received set of bio-signals.

19 Claims, 8 Drawing Sheets

(51) Int. Cl.
*G16H 30/20* (2018.01)
*G16H 50/20* (2018.01)
*G16H 30/40* (2018.01)
*A61B 5/00* (2006.01)
*G06F 3/01* (2006.01)
*G06T 15/08* (2011.01)

(52) U.S. Cl.
CPC .......... *A61B 5/7445* (2013.01); *A61B 5/7455* (2013.01); *G06F 3/016* (2013.01); *G06T 15/08* (2013.01); *G16H 30/20* (2018.01); *G16H 30/40* (2018.01); *G16H 50/20* (2018.01); *G16H 50/50* (2018.01); *A61B 5/0002* (2013.01); *A61B 5/445* (2013.01); *A61B 5/4504* (2013.01); *G06T 2210/41* (2013.01)

(56) References Cited

U.S. PATENT DOCUMENTS

| | | | |
|---|---|---|---|
| 8,638,308 | B2 | 1/2014 | Cunningham et al. |
| 10,108,266 | B2 * | 10/2018 | Banerjee ................ G09B 23/30 |
| 10,698,493 | B1 * | 6/2020 | Crowther ................ A61B 34/37 |
| 2010/0274447 | A1 | 10/2010 | Stumpf |
| 2020/0126297 | A1 | 4/2020 | Tian et al. |

FOREIGN PATENT DOCUMENTS

| | | |
|---|---|---|
| CN | 111986316 A | 11/2020 |
| EP | 1582145 A2 | 10/2005 |
| GB | 2574849 A | 12/2019 |
| WO | 2004/037084 A1 | 5/2004 |
| WO | 2012/101286 A1 | 8/2012 |
| WO | 2019/051464 A1 | 3/2019 |
| WO | 2019/243828 A1 | 12/2019 |
| WO | 2020/078292 A1 | 4/2020 |

OTHER PUBLICATIONS

International Search Report and Written Opinion of PCT Application No. PCT/IB2021/060104, dated Jan. 31, 2022, 12 pages of ISRWO.

Filippeschi, et al., "Encountered-type haptic interface for virtual interaction with real objects based on implicit surface haptic rendering for remote palpation", IEEE/RSJ International Conference on Intelligent Robots and Systems (IROS), XP032832437, Sep. 28, 2015, pp. 5904-5909.

Hernandez-Ossa, et al., "Haptic Feedback for Remote Clinical Palpation Examination", 2nd International Workshop on Assistive Technology (IWAT2019), XP055881625, Feb. 1, 2019, 4 pages.

* cited by examiner

US 11,776,687 B2

1

MEDICAL EXAMINATION OF HUMAN BODY USING HAPTICS

CROSS-REFERENCE TO RELATED APPLICATIONS/INCORPORATION BY REFERENCE

None.

FIELD

Various embodiments of the disclosure relate to telemedicine and virtual reality technology. More specifically, various embodiments of the disclosure relate to an electronic apparatus and a method for medical examination of human body using haptics.

BACKGROUND

Advancements in medical technology have paved way for various health and medical services, such as telemedicine and remote surgery. Due to this, some of conventional medical practices, such as physical examination of patients appears to be on its way out in contemporary medicine. Less experienced medical practitioners may have a limited access to different type of patients to examine or learn symptoms and perform diagnosis using touch.

Limitations and disadvantages of conventional and traditional approaches will become apparent to one of skill in the art, through comparison of described systems with some aspects of the present disclosure, as set forth in the remainder of the present application and with reference to the drawings.

SUMMARY

An electronic apparatus and method for a medical examination of a human body using haptics, are provided substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Figure 1:
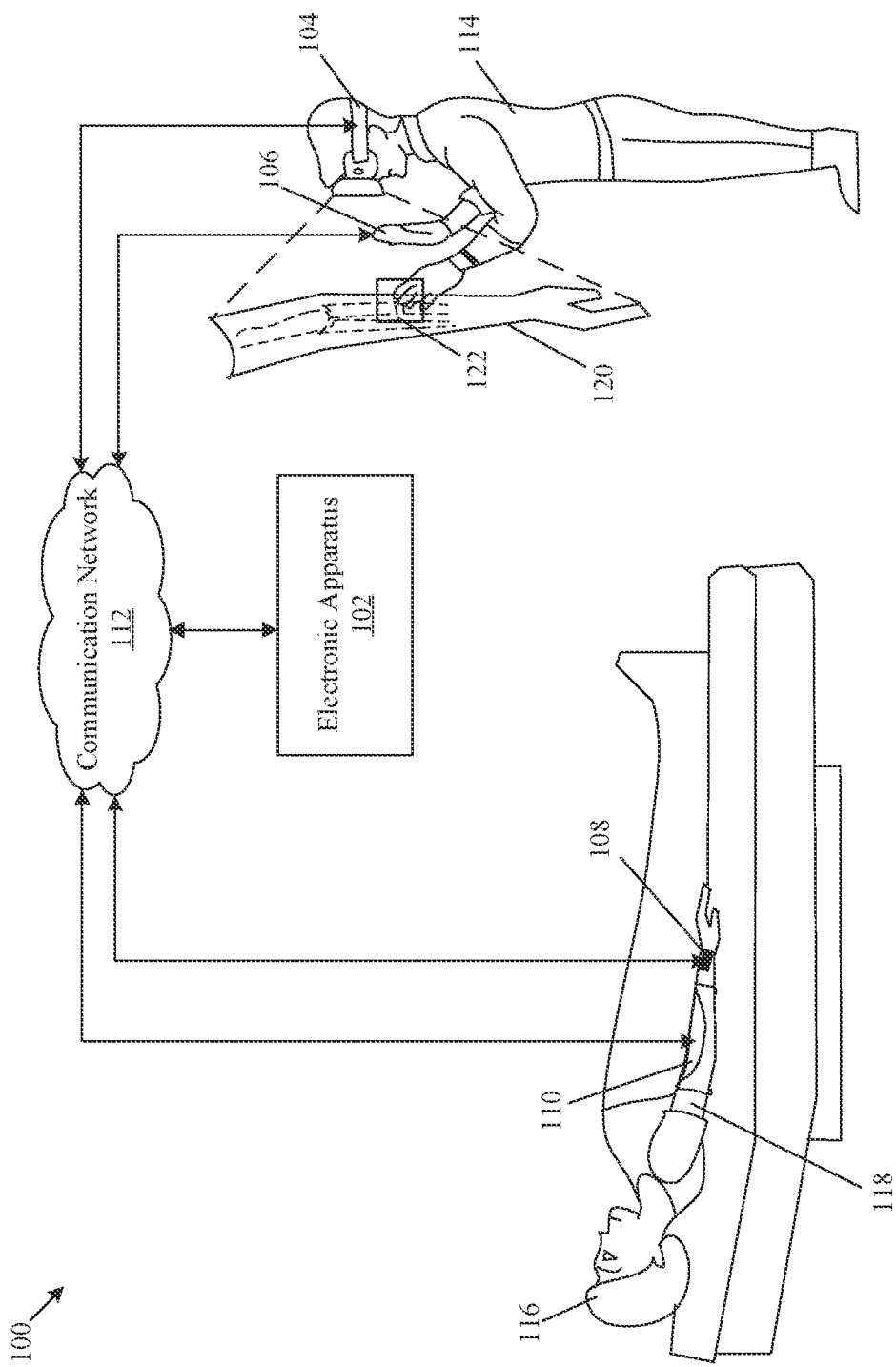
FIG. 1 is a diagram of an exemplary network environment for medical examination of human body using haptics, in accordance with an embodiment of the disclosure.

The following described implementations may be found in the disclosed electronic apparatus and a method for a medical examination of human body using haptics. Exemplary aspects of the disclosure provide an electronic apparatus that may be configured to control a first head-mounted display (such as a virtual reality headset) to render a first three-dimensional (3D) model of at least a first anatomical portion (such as an arm) of a body of a human subject (who may be a patient). The rendered first 3D model may include a first region corresponding to a defect portion in the first anatomical portion of the body. For example, the defect portion may correspond to a bone fracture in the arm of the body of the human subject.

At any time-instant, a medical practitioner, while wearing the head-mounted display, may touch the first region of the rendered first 3D model to examine the defect portion in the first anatomical portion of the body of the human subject. In response to the touch, the electronic apparatus 102 may transmit a touch input to a wearable sensor in contact with at least the first anatomical portion of the body. The wearable sensor may receive the touch input and may transmit a set of bio-signals associated with the defect portion, to the electronic apparatus. The wearable sensor may extract the set of bio-signals based on acquisition of physiological datapoints (such as heart rate) and somatic sensation information from the defect portion of the body.

The electronic apparatus may receive the transmitted set of bio-signals via the wearable sensor. The set of bio-signals may include physiological signals (such as heart rate) associated with the defect portion and somatic sensation information (such as sensation associated with touch, pressure, cold, or warmth) associated with the defect portion. The electronic apparatus may control a wearable haptic device (such as a wearable glove worn by the medical practitioner) to generate a haptic feedback based on the received set of bio-signals. The haptic feedback may be generated as a response to the human touch on the first region of the first 3D model.

The electronic apparatus may enable the medical practitioner to physically examine any defect portion of the human subject in a remote consultation setup. In some scenarios, the electronic apparatus may also enable a medical practitioner or a trainee in medicine to learn aspects of physical examination and medical consultation by interacting with 3D models of several test subjects or patients, whose medical records, bio-signals from different portions of the body, and 3D scan data may be stored on a server.

While the head-mounted display may enable the medical practitioner to view and interact with a 3D model of an anatomical portion of a human subject, the wearable haptic device may enable the medical practitioner to feel touch sensations and other somatic sensations associated with the defect portion. For example, such sensations may emulate a feeling of cold or warmth, a tactile sensation, or a pressure which may be typically experienced when a medical practitioner uses his/her hand to touch and apply a pressure on a portion of body. In contrast with a traditional video-based consultation, the electronic apparatus of the present disclosure may enhance a remote consultation experience of both the medical practitioner and the patient and may help the medical practitioner to perform a better diagnosis and/or prognosis of any ailment or medical condition of the patient.

In order to further enhance a remote consultation experience, a haptic device in contact with the first anatomical portion of patient's body may generate a haptic feedback on the defect portion of the body. The haptic feedback may help the patient to feel a tactile or touch sensation in response to a touch applied by the medical practitioner to the first region of the rendered 3D model. The electronic apparatus may implement a machine learning model to generate recommendations for the medical practitioner. Such recommendations may be based on the received set of bio-signals, medical condition information associated with the human subject, and anthropometric features related to the body of the human subject. For example, such recommendations may include, but are not limited to, a course of treatment for the defect portion, a current condition of the defect portion, a prognosis for the defect portion, and a diagnosis related to the defect portion of the human subject.

FIG. 1 is a diagram of an exemplary network environment for medical examination of human body using haptics, in accordance with an embodiment of the disclosure. With reference to FIG. 1, there is shown a block diagram of a network environment 100. The network environment 100 may include an electronic apparatus 102, a first head-mounted display 104, a wearable haptic device 106, a wearable sensor 108, and a haptic device 110. The electronic apparatus 102, the first head-mounted display 104, the wearable haptic device 106, the wearable sensor 108, and the haptic device 110 may communicate with each other via the communication network 112. The network environment 100 is merely shown as an example environment for a remote medical examination (or consultation) and should not be construed as limiting for the disclosure.

In the network environment 100, a user 114, such as a medical practitioner or a trainee in medicine is shown wearing the first head-mounted display 104 and the wearable haptic device 106. Also, a human subject 116 (who may be a patient) is shown with the wearable sensor 108 in contact with at least a first anatomical portion 118 of the body of the human subject 116. In an embodiment, at least the first anatomical portion 118 of the body may be in contact with the haptic device 110.

The electronic apparatus 102 may include suitable logic, circuitry, and interfaces that may be configured to control the first head-mounted display 104 to render a first three-dimensional (3D) model 120 of at least the first anatomical portion 118 of the body of the human subject 116. The electronic apparatus 102 may be further configured to receive, based on a touch input, a set of bio-signals associated with a defect portion in the first anatomical portion 118 of the body. Examples of the electronic apparatus 102 may include, but are not limited to, a computing device, a smartphone, a cellular phone, a mobile phone, a gaming device, a mainframe machine, a server, a computer workstation, and/or a consumer electronic (CE) device.

In an embodiment, the electronic apparatus 102 may be implemented as a head-mounted apparatus which may be worn by the user 114. In such an implementation, the first head-mounted display 104 may be integrated with the head-mounted apparatus. An example implementation of the head-mounted apparatus may include, but are not limited to, smart glasses, a virtual reality (VR) headset, an augmented reality (AR) headset, or a mixed reality (MR) headset.

The first head-mounted display 104 may include suitable logic, circuitry, and interfaces that may be configured to render the first 3D model 120 of at least the first anatomical portion 118 of the body of the human subject 116. The first head-mounted display 104 may be worn on the head or as part of a helmet by the user 114 (such as a medical practitioner). The first head-mounted display 104 may include a display optic, such that the display optic is placed in front of one or both eyes of the user 114, when the user 114 wears the first head-mounted display 104. In an embodiment, the first head-mounted display 104 may include an inertial measurement unit for a VR experience of the user 114. Examples of the first head-mounted display 104 may include, but are not limited to, a virtual reality headset, an optical head-mounted display, an augmented reality headset, a mixed reality headset, virtual reality glasses, virtual reality eye lens.

The wearable haptic device 106 may include suitable logic, circuitry, and interfaces that may be configured to generate a haptic feedback based on a set of bio-signals associated with a defect portion in the first anatomical portion 118 of the body of the human subject 116. Shown as an example, the wearable haptic device 106 may be worn by the user 114 (such as the medical practitioner) on one or both hands of the user 114. The haptic feedback may be generated as a response to a human touch of the user 114 on the first region 122 of the first 3D model 120. In an embodiment, the wearable haptic device 106 may include sensors, such as tactile sensors that may allow measurement of force of the human touch of the user 114 on the first region 122 of the first 3D model 120. Examples of the wearable haptic device 106 may include, but are not limited to, a haptic glove, a wired glove with haptic actuators, a gaming glove with haptic actuators, a wearable fingertip haptic device (such as a haptic thimble or a touch thimble), a graspable haptic device (which may generate kinesthetic sensations, such as a sensation of movement, position and force in skin, muscles, tendons, and joints of a wearer), or a wearable device (which generates tactile sensations, such as a pressure, friction, or temperature in the skin of a wearer), joysticks with haptic actuators, mouse, finger pad, robotic handle, gripper and a humanoid robotic hand with haptic actuators.

The wearable sensor 108 may include suitable logic, circuitry, and interfaces that may be configured to receive a touch input from the electronic apparatus 102. The received touch input may correspond to a human touch of the user 114 (such as the medical practitioner) on the first region 122 of the first 3D model 120. The wearable sensor 108 may be configured to measure one or more parameters associated with the human subject 116 to produce a set of bio-signals. Based on the touch input, the wearable sensor 108 may transmit the set of bio-signals to the electronic apparatus 102. The set of bio-signals may include physiological signals and somatic sensation information associated with a defect portion (for example, a fractured bone) in the first anatomical portion 118 of the body of the human subject 116. The set of bio-signals may include for example, an electroencephalogram (EEG) of the human subject 116, an electrocardiogram (ECG) of the human subject 116, an electromyogram (EMG) of the human subject 116, a galvanic skin response (GSR) of the human subject 116, and the like.

In an embodiment, the wearable sensor 108 may be in contact with at least the first anatomical portion 118 of the body of the human subject 116. In another embodiment, the wearable sensor 108 may be a wrapped, wound, or strapped around the first anatomical portion 118 of the body. The wearable sensor 108 may acquire multi-modal data through sensors, such as, but not limited to, a photoplethysmography (PPG) sensor, a temperature sensor, a blood pressure sensor, an ambient oxygen partial pressure (ppO2) sensor, or sensors which collect the somatic sensation information associated with the first anatomical portion 118 of the body. Example implementations of the wearable sensor 108 may include, but are not limited to, a belt-type wearable sensor, a vest with embedded bio-sensors, a waist strap with embedded bio-sensors, a wrist strap with embedded bio-sensors, an instrumented wearable belt, a wearable garment with embedded bio-sensors, or a wearable article-of-manufacture having a retrofitting of bio-sensors.

The haptic device 110 may include suitable logic, circuitry, and interfaces that may be configured to reproduce a sensation of a human touch on any specific location of the first anatomical portion 118. The sensation may be reproduced as a haptic sensation by the haptic device 110 and may be reproduced based on the touch input (i.e. a human touch by the user 114) on the first region 122 of the first 3D model 120. The haptic device 110 may be configured to be worn by the human subject 116. For example, the haptic device 110 may be in contact with at least the first anatomical portion 118 of the body of the human subject 116. Examples of the haptic device 110 may include, but are not limited to, a wearable garment with haptic actuators, a wearable device with haptic actuators, or any device in a form of a wearable belt or medical tape/cloth with haptic actuators. In an embodiment, the haptic device 110 may be integrated or embedded into the wearable sensor 108.

The communication network 112 may include a communication medium through which the electronic apparatus 102, the first head-mounted display 104, the wearable haptic device 106, the wearable sensor 108, and the haptic device 110 may communicate with each other. Examples of the communication network 112 may include, but are not limited to, the Internet, a cloud network, a Wireless Fidelity (Wi-Fi) network, a Personal Area Network (PAN), a Local Area Network (LAN), or a Metropolitan Area Network (MAN). Various devices in the network environment 100 may be configured to connect to the communication network 112, in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols.

In operation, the electronic apparatus 102 may initialize a session on the first head-mounted display 104. The session may be a remote consultation session between the user 114, such as a medical practitioner and the human subject 116. The session may include a medical examination (for example, a physical examination in a computer-simulated environment) of at least the first anatomical portion 118 of the body of the human subject 116.

The electronic apparatus 102 may generate the first 3D model 120 of at least the first anatomical portion 118 of the body of the human subject 116 based on 3D scan data of at least the first anatomical portion 118 of the body. The 3D scan data may be acquired in near-real time from camera-rig or may be stored in a medical database. In some embodiment, the first 3D model 120 may be generated further based on anthropometric features (such as skin color, skin texture, weight, height, or age) related to the body of the human subject 116. In these or other embodiment, the first 3D model 120 may be generated based on appearance attributes associated with the defect portion in the first anatomical portion 118 of the body of the human subject 116. The appearance attributes may be used to determine a modification to be made to the first 3D model 120 to show the defect portion.

After the session is initialized, the electronic apparatus 102 may control the first head-mounted display 104 to render the first 3D model 120 of at least the first anatomical portion 118 of the body of the human subject 116. As an example, the first 3D model 120 may be a computer-generated model and may be rendered in a computer-simulated environment, such as a VR environment or an AR environment. The first 3D model 120 may include the first region 122 that may correspond to a defect portion in the first anatomical portion 118 of the body. Examples of the defect portion may include, but are not limited to, a tissue deformation or defect, a bruised tissue or skin, a fractured bone, a tumorous tissue or organ, a deformed bone, or a swelling or lump.

The first head-mounted display 104 may be associated with the user 114, such as the medical practitioner that may utilize the first head-mounted display 104 to view and examine at least the first anatomical portion 118 of the body of the human subject 116. The first anatomical portion 118 of the body may include, for example, a hand, arm, legs, abdomen, torso, head, bones, or internal organ(s), skin, muscles, tendons, or a combination thereof. Details of the control of the first head-mounted display 104 to render the first 3D model 120 are provided, for example, in FIG. 4.

At any time-instant, the user 114, such as a medical practitioner, while wearing the first head-mounted display 104, may touch the first region 122 of the rendered first 3D model 120 to examine the defect portion in the first anatomical portion 118 of the body of the human subject 116. In response to the touch, the electronic apparatus 102 may transmit a touch input to the wearable sensor 108 that may be in contact with at least the first anatomical portion 118 of the body of the human subject 116. The transmitted touch input may correspond to a human touch (for example, by the user 114) on the first region 122 of the rendered first 3D model 120. For example, the touch input may activate the wearable sensor 108 to measure the one or more parameters associated with the human subject 116, such as, but not limited to, the body temperature, somatic sensations (which includes touch sensations, such as tactile or kinesthetic sensations) associated with the defect portion, and the blood pressure of the human subject 116. Details of the transmission of the touch input to the wearable sensor 108 are provided, for example, in FIG. 4.

The electronic apparatus 102 may receive a set of bio-signals from the wearable sensor 108, via the communication network 112. The set of bio-signals may be transmitted based on the touch input and may be associated with the defect portion in the first anatomical portion 118 of the body of the human subject 116. The set of bio-signals may include physiological signals and somatic sensation information associated with the defect portion in the first anatomical portion 118 of the body. Details associated with a reception of the touch input from the wearable sensor 108 are provided for example, in FIG. 4.

The electronic apparatus 102 may control the wearable haptic device 106 to generate a haptic feedback based on the received set of bio-signals. The haptic feedback may be generated as a response to the human touch (such as of the user 114) on the first region 122 of the first 3D model 120. Details of the generation of the haptic feedback are further provided for example, in FIG. 4.

While the first head-mounted display 104 may enable the user 114, who may be a medical practitioner, to view and interact with the first 3D model 120 of at least the first anatomical portion 118 of the human subject 116, the wearable haptic device 106 may enable the user 114 to feel touch sensations and other somatic sensations associated with the defect portion. For example, such sensations may emulate a feeling of cold or warmth, a tactile sensation, or a pressure which may be typically experienced when a medical practitioner uses his/her hand to touch and apply a pressure on a portion of body. In contrast with a traditional video-based consultation, the electronic apparatus 102 of the present disclosure may enhance a remote consultation experience of both the medical practitioner and the patient and may help the medical practitioner to perform a better diagnosis and/or prognosis of any ailment or medical condition of the patient.

Figure 2:
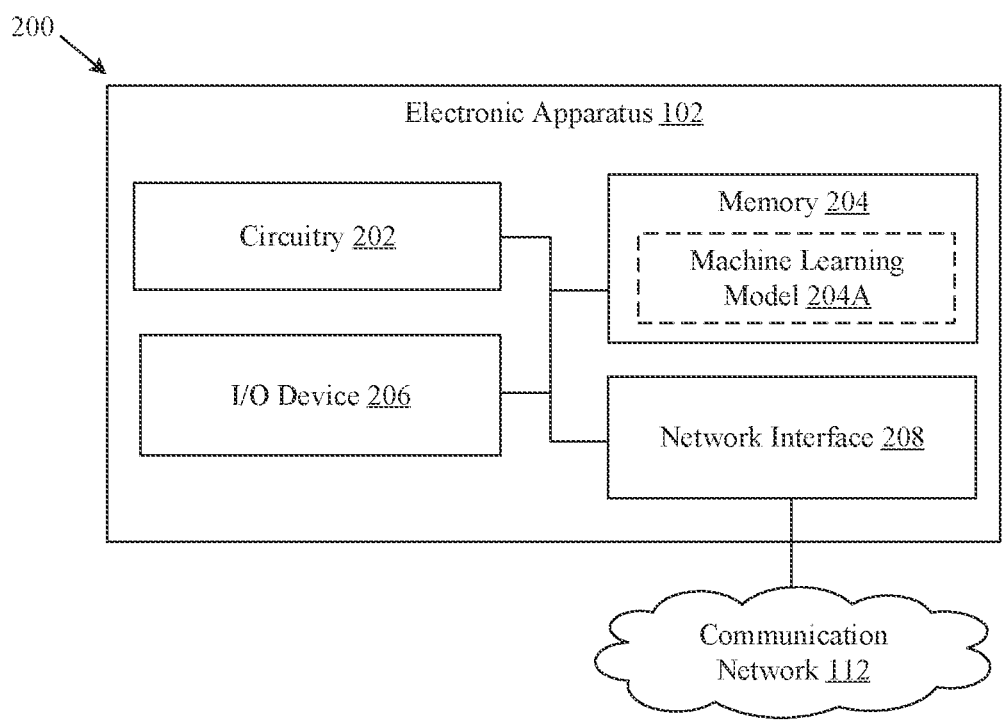
FIG. 2 is a block diagram of an electronic apparatus for a medical examination of human body using haptics, in accordance with an embodiment of the disclosure.

FIG. 2 is a block diagram of an electronic apparatus for a medical examination of human body using haptics, in accordance with an embodiment of the disclosure. FIG. 2 is explained in conjunction with elements from FIG. 1. With reference to FIG. 2, there is shown a block diagram 200 of the electronic apparatus 102 of FIG. 1. The electronic apparatus 102 may include circuitry 202 and a memory 204. The memory 204 may include a machine learning model 204A. The electronic apparatus 102 may further include an input/output (I/O) device 206 and a network interface 208. In an embodiment, the electronic apparatus 102 may include the first head-mounted display 104 as a display unit of the electronic apparatus 102.

The circuitry 202 may include suitable logic, circuitry, and interfaces that may be configured to execute program instructions associated with different operations to be executed by the electronic apparatus 102. The circuitry 202 may include one or more specialized processing units, which may be implemented as an integrated processor or a cluster of processors that perform the functions of the one or more specialized processing units, collectively. The circuitry 202 may be implemented based on a number of processor technologies known in the art. Examples of implementations of the circuitry 202 may be an x86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), a co-processor, or a combination thereof.

The memory 204 may include suitable logic, circuitry, and interfaces that may be configured to store the program instructions to be executed by the circuitry 202. The memory 204 that may be configured to store the first 3D model 120 of the human subject 116 and the machine learning model 204A. The memory 204 may be further configured to store a first set of features which include the anthropometric features related to the body, medical information associated with the human subject 116, and a second set of features related to the defect portion of the body of the human subject 116. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The machine learning model 204A may be a recommendation model which may be trained to identify a relationship between input features and medical recommendations. The input features may include, for example, features obtained from a set of bio-signals, medical condition information, and/or medical records of the human subject 116. The machine learning model 204A may be defined by its hyper-parameters, for example, a number of weights, a cost function, an input size, a number of layers as defined by a topology, and the like. The hyper-parameters of the machine learning model 204A may be tuned and weights may be updated so as to move towards a global minimum of a cost function for the machine learning model 204A. After several epochs of the training on features in a training dataset, the machine learning model 204A may be trained to output a result for a given input feature. For example, the result may be used to select a recommendation from a database of recommendations which may be provided for different medical conditions or symptoms. After the wearable haptic device 106 generates the haptic feedback, the recommendation may be presented to the human subject 116 as a medical advice or a consultation.

The machine learning model 204A may include electronic data, which may be implemented as, for example, a software component of an application executable on the electronic apparatus 102 (or the first head-mounted display 104). The machine learning model 204A may rely on libraries, external scripts, or other logic/instructions for execution by a processing device, such as the electronic apparatus 102. The machine learning model 204A may include code and routines configured to enable a computing device, such as electronic apparatus 102 to perform one or more operations to output a recommendation based on one or more inputs. Additionally, or alternatively, the machine learning model 204A may be implemented using hardware including a processor, a microprocessor (e.g., to perform or control performance of one or more operations), a field-programmable gate array (FPGA), or an application-specific integrated circuit (ASIC). Alternatively, in some embodiments, the machine learning model 204A may be implemented using a combination of hardware and software.

Examples of the machine learning model 204A may include, but are not limited to, a linear regression algorithm, a logistic regression algorithm, a decision tree algorithm, a Support Vector Machine (SVM) algorithm, a naive Bayes algorithm, a random forest algorithm, and a K-nearest neighbor (KNN) algorithm. In an embodiment, the machine learning model 204A may be implemented as a neural network. Examples of the neural network may include, but are not limited to, a deep neural network (DNN), a convolutional neural network (CNN), a recurrent neural network (RNN), a CNN-recurrent neural network (CNN-RNN), Region-based CNN (R-CNN), Fast R-CNN, Faster R-CNN, an artificial neural network (ANN), (You Only Look Once) YOLO network, a Long Short Term Memory (LSTM) network based RNN, CNN+ANN, LSTM+ANN, a gated recurrent unit (GRU)-based RNN, a fully connected neural network, a Connectionist Temporal Classification (CTC) based RNN, a deep Bayesian neural network, a Generative Adversarial Network (GAN), and/or a combination of such networks. In some embodiments, the machine learning model 204A may implement numerical computation techniques using data flow graphs. In certain embodiments, the machine learning model 204A may be based on a hybrid architecture of multiple Deep Neural Networks (DNNs).

The I/O device 206 may include suitable logic, circuitry, and interfaces that may be configured to receive an input from the user 114, who may be a medical practitioner and provide an output based on the received input. The I/O device 206 which may include various input and output devices, may be configured to communicate with the circuitry 202. Examples of the I/O device 206 may include, but are not limited to, a touch screen, a keyboard, a mouse, a joystick, a microphone, a display device, and a speaker.

The network interface 208 may include suitable logic, circuitry, and interfaces that may be configured to facilitate communication between the electronic apparatus 102 and the first head-mounted display 104, the wearable haptic device 106, the wearable sensor 108 and the haptic device 110, via the communication network 112. The network interface 208 may be implemented by use of various known technologies to support wired or wireless communication of the electronic apparatus 102 with the communication network 112. The network interface 208 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry. The network interface 208 may be configured to communicate via wireless communication with networks, such as the Internet, an Intranet or a wireless network, such as a cellular telephone network, a wireless local area network (LAN), and a metropolitan area network (MAN). The wireless communication may be configured to use one or more of a plurality of communication standards, protocols and technologies, such as New Radio $5^{th}$ Generation (5G NR), Global System for Mobile Communications (GSM), Enhanced Data GSM Environment (EDGE), wideband code division multiple access (W-CDMA), Long Term Evolution (LTE), code division multiple access (CDMA), time division multiple access (TDMA), Bluetooth, Wireless Fidelity (Wi-Fi) (such as IEEE 802.11a, IEEE 802.11b, IEEE 802.11g or IEEE 802.11n), voice over Internet Protocol (VoIP), light fidelity (Li-Fi), Worldwide Interoperability for Microwave Access (Wi-MAX), a protocol for email, instant messaging, and a Short Message Service (SMS).

The functions or operations executed by the electronic apparatus 102, as described in FIG. 1, may be performed by the circuitry 202. Operations executed by the circuitry 202 are described in detail, for example, in FIG. 3, FIG. 4, FIG. 5, FIG. 6, and FIG. 7.

Figure 3:
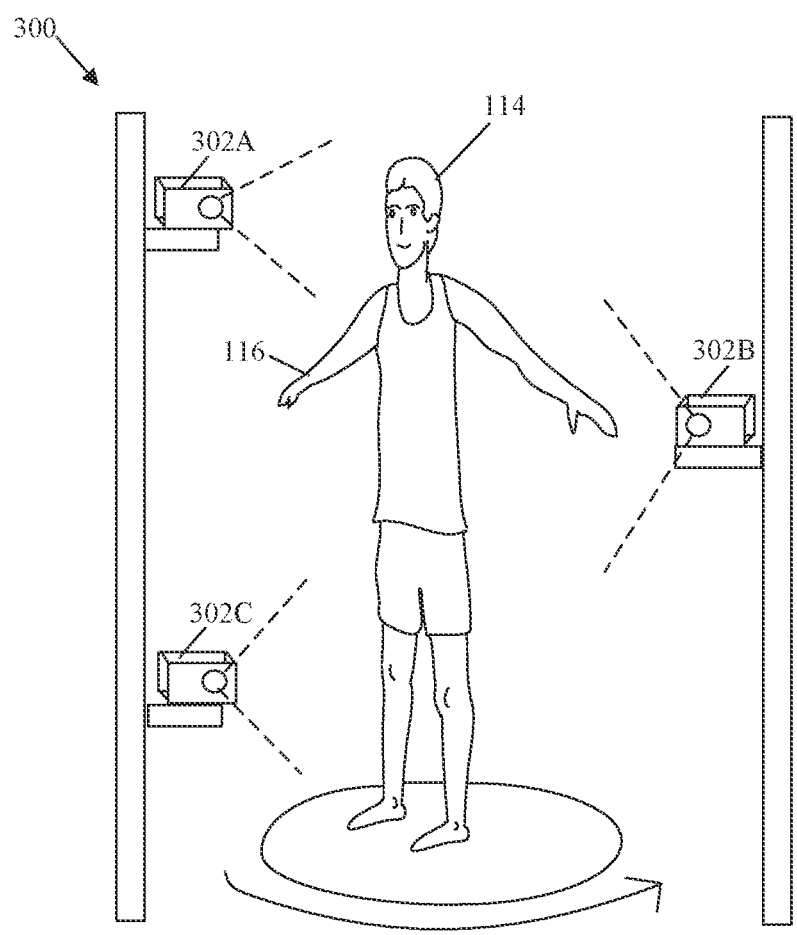
FIG. 3 is a diagram that illustrates an exemplary scenario for a 3D scan of a human subject using a camera rig, in accordance with an embodiment of the disclosure.

FIG. 3 is a diagram that illustrates an exemplary scenario for a 3D scan of a human subject using a camera rig, in accordance with an embodiment of the disclosure. FIG. 3 is described in conjunction with elements from FIGS. 1 and 2. With reference to FIG. 3, there is shown a scenario 300. In the scenario 300, there is shown a camera rig that may include one or more imaging sensors, such as a first imaging sensor 302A, a second imaging sensor 302B, and a third imaging sensor 302C. In the scenario 300, the human subject 116 is shown to have a T-posture on a scanning spot associated with the camera rig. The disclosure may be applicable other postures of the human subject 116 for a 3D scan.

In an embodiment, the one or more imaging sensors may be depth sensors (such as a Time-of-Flight sensor) that may be configured to scan the human subject 116 to capture physical features of the human subject 116 in detail, such as skin color, skin texture and hair on a body of the human subject 116. In accordance with an embodiment, the circuitry 202 may be configured to control the camera rig (that includes the one or more imaging sensors) to scan at least the first anatomical portion 118 of the body of the human subject 116. The camera rig may execute a 3D scan of at least the first anatomical portion of the human subject 116 to capture the physical features in detail. The one or more imaging sensors may be connected to a single target machine to perform the scan of the human subject 116. In some embodiments, the one or more imaging sensors may be connected to multiple target machines to perform the scan of the human subject 116.

As shown in FIG. 3, the first imaging sensor 302A may be placed such that the first imaging sensor 302A scans at least an upper portion of the body of the human subject 116. The second imaging sensor 302B may be placed such that the second imaging sensor 302B scans at least a middle portion of the body of the human subject 116. The third imaging sensor 302C may be placed such that the third imaging sensor 302C scans at least a lower portion of the body of the human subject 116. In the scenario 300, there is shown a platform on which the human subject 116 may stand for a 3D scan. The platform may be rotatable such that the camera rig may execute the 3D scan of the human subject 116 from multiple viewpoints. In an embodiment, the circuitry 202 (or the camera rig) may register viewpoint-specific scan data from all such viewpoints into 3D scan data.

The one or more imaging sensors may be configured to scan the body of the human subject 116, for example, at a hospital, at home of the human subject 116, or a specific location (e.g. a scan studio) for the scan of the body of the human subject 116.

In some embodiments, imaging data from at least one surgical-assistive device (such as laparoscope, X-ray, or ultrasound) may be acquired. Such imaging data may include, for example, images and depth information associated with one or more internal organs of the human subject 116. The circuitry 202 may generate a 3D representation of one or more internal organs (with or without the defect portion) of the human subject 116 based on such imaging data. In these or other embodiments, the circuitry 202 may fuse the 3D scan data from the camera rig with the generated 3D representation.

In an embodiment, the circuitry 202 may be configured to receive depth information associated with the defect portion from the one or more imaging sensors. For example, the circuitry 202 may receive the depth information (which may also include texture, reflectance, or albedo information) related to an amount of swelling in the defect portion due to a fractured bone of the human subject 116. Based on the received depth information, the circuitry 202 may generate the first region 122 of the first 3D model 120, corresponding to the defect portion in the first anatomical portion 118 of the body. The first region 122 may be rendered as part of the first 3D model 120. For example, the first region 122 may be rendered to model the defect portion, such as a fractured bone in the first anatomical portion 118 (such as the arm) of the body of the human subject 116.

The circuitry 202 may be configured to receive the 3D scan data of at least the first anatomical portion 118 of the body based on a 3D scan by the one or more imaging sensors (of the camera rig). The 3D scan data may include the depth information associated with the defect portion in the first anatomical portion 118 of the body. In accordance with an embodiment, the 3D scan data may include a 3D representation of at least one internal organ of the human subject 116.

The 3D representation of at least one internal organ may be generated based on, for example, a scan performed by a laparoscope camera. The defect portion may be depicted in the 3D representation as a swelling or a lump in internal tissues or at least one internal organ, such as lungs, kidneys, or stomach. The circuitry 202 may be configured to control the first head-mounted display 104 to render the first 3D model 120 of at least the first anatomical portion 118 of the body based on the received 3D scan data. Details associated with a rendering operation of the first 3D model 120 are further provided, for example, in FIG. 4.

Figure 4:
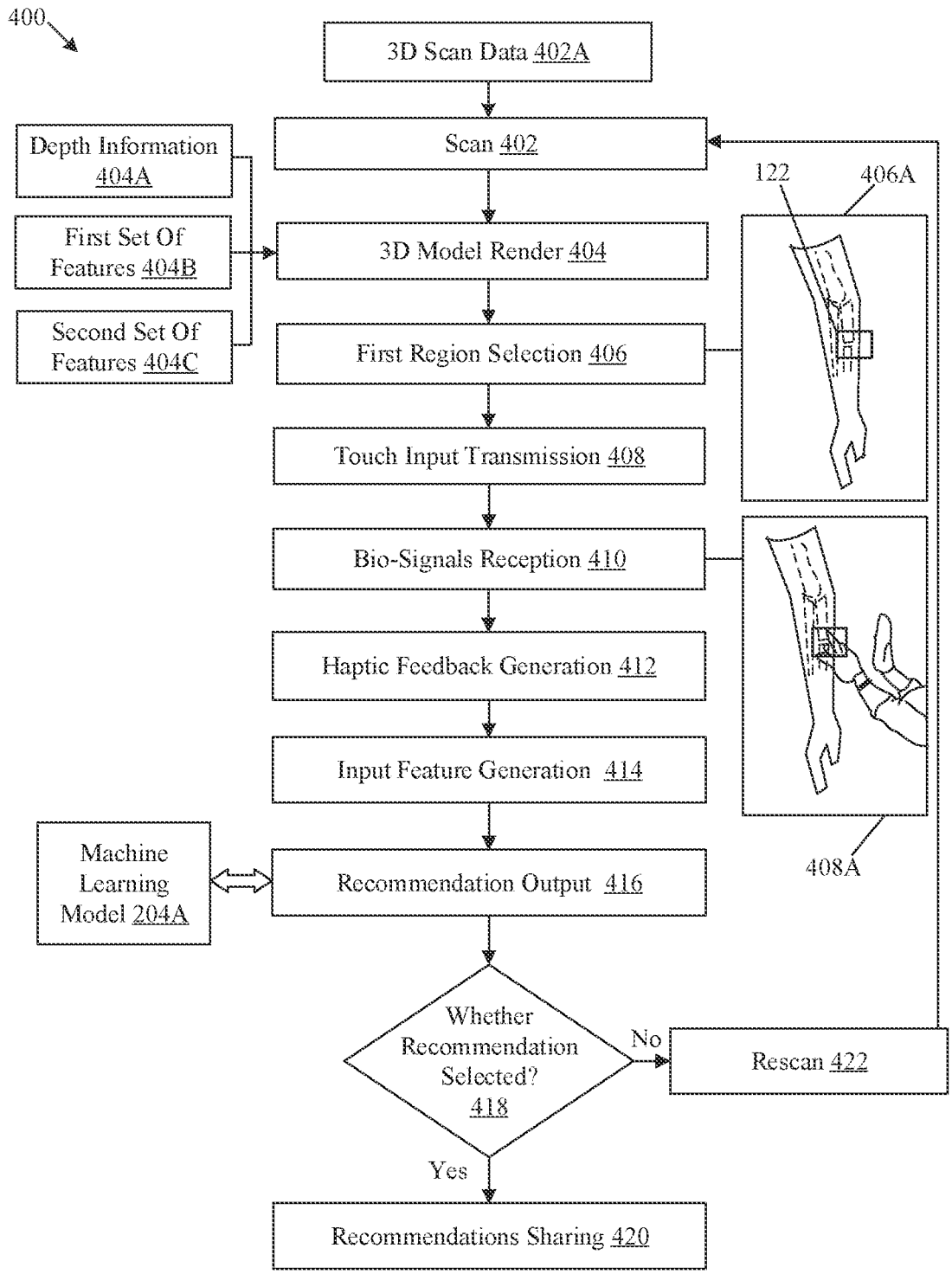
FIG. 4 is a diagram that illustrates exemplary operations for medical examination of a human body using haptics, in accordance with an embodiment of the disclosure.

FIG. 4 is a diagram that illustrates exemplary operations for medical examination of a human body using haptics, in accordance with an embodiment of the disclosure. FIG. 4 is explained in conjunction with elements from FIGS. 1, 2, and 3. With reference to FIG. 4, there is shown a diagram 400 to depict exemplary operations from 402 to 422. The exemplary operations illustrated in the diagram 400 may start at 402 and may be performed by any computing system, apparatus, or device, such as by the electronic apparatus 102 of FIG. 2.

At 402, a scan of the human subject 116 may be executed. In accordance with an embodiment, the circuitry 202 may be configured to control the camera rig (as shown in FIG. 3, for example) to scan at least the first anatomical portion 118 of the body of the human subject 116 and receive 3D scan data 402A of at least the first anatomical portion of the body of the human subject from the camera rig, based on the scan. The scan of the human subject 116 may have to be executed before a remote consultation session or a remote medical examination can be initiated. In some embodiments, the scan may be executed more than once before and/or within a duration of one or more remote consultation sessions. For example, if a person has a fracture on knees, then a scan may be executed before a first remote consultation session is started and another 3D scan may be executed before a follow-up consultation session is started to check for a recovery of the fracture and decide for future course of treatment.

At 404, the first 3D model 120 may be rendered on the first head-mounted display 104. In accordance with an embodiment, the circuitry 202 may be configured to control the first head-mounted display 104 to render the first 3D model 120 of at least the first anatomical portion 118 of the body of the human subject 116. Before rendering, the first 3D model 120 may be generated based on the 3D scan data (such as 3D scan data 402A) of the first anatomical portion 118 of the body, the depth information (such as depth information 404A), a first set of features 404B, and a second set of features 404C.

In one or more embodiments, the depth information 404A may be associated with the defect portion and may be received from the one or more imaging sensors (as described in FIG. 3). For example, the depth information 404A may be associated with an amount of swelling in the arm of the human subject 116 due to a fracture of the bone in the first anatomical portion 118 of the body. The 3D scan data 402A may be received based on the scan executed by the camera rig (that includes the one or more imaging sensors). The 3D scan data 402A may include details, such as the body shape, skin texture, albedo information for the body, skin shade associated with at least the first anatomical portion 118 of the body of the human subject 116.

In accordance with an embodiment, the circuitry 202 may be configured to receive the first set of features 404B. The first set of features 404B may include anthropometric features related to the body of the human subject 116 and medical condition information associated with the human subject 116. The anthropometric features may relate to quantitative measurements associated with the body of the human subject 116. Examples of the anthropometric features associated with the human subject 116 may include, but are not limited to, a height of the human subject 116, a weight of the human subject 116, a body mass index (BMI) of the human subject 116, size measurements (for example, a chest measurement, a waist measurement, a hip measurement, or a limb size measurement) of different parts of the body, and a skinfold thickness. Similarly, the medical condition information associated with the human subject 116 may include, for example, a medical history of medical treatments, surgeries, trauma, or injuries, prior health conditions (for example, varicose veins), vital health statistics (such as Blood Pressure (BP) or Iron levels in blood), test report information (for example, a blood test report), other test-related information (such as a pathology report). The test report information may include for example, an X-ray report, a Magnetic resonance imaging (MRI) report associated with at least the first anatomical portion 118 of the body, and the like. The first 3D model 120 may be generated based on the first set of features 404C for an accurate depiction of the physical features of the human subject 116 in the first 3D model 120. After the first 3D model 120 is generated, the first 3D model 120 may be rendered on the first head-mounted display 104.

In accordance with an embodiment, the circuitry 202 may be configured to receive the second set of features 404C. Such features may be related to the defect portion in the first anatomical portion 118 of the body of the human subject 116 and may include appearance attributes associated with the defect portion. In some embodiments, the second set of features 404C may include physical deformities associated with at least the first anatomical portion 118 of the body or deformities associated with one or more internal organs of the body. As an example, the second set of features 404C may specify a swelling (i.e. a deformation) in the defect portion due to a fractured bone and a redness of the skin around the swelling. As another example, the second set of features 404C may specify a lump or cyst in an internal organ (such as on liver) of the human subject 116. The defect portion in the first 3D model 120 may be generated based on the second set of features 404C.

In accordance with an embodiment, the circuitry 202 may be configured to update the generated first 3D model 120 by a mesh deformation of at least the first region 122 of the generated first 3D model 120. The mesh deformation may be applied based on the received second set of features 404C to model the appearance of the defect portion in the first region 122 of the first 3D model 120. The first head-mounted display 104 may render the updated first 3D model 120 based on control signals from the circuitry 202.

At 406, the first region 122 may be selected. In accordance with an embodiment, the circuitry 202 may be configured to select the first region 122 in the rendered first 3D model 120 of the first anatomical portion 118, as shown in a view 406A. The first region 122 may correspond to the defect portion in the first anatomical portion 118 of the body. The first region 122 may be selected by the user 114 (such as the medical practitioner) for a medical examination of the human subject 116. By way of example, and not limitation, the defect portion may be one or more of: a tissue deformation or defect, a bruised tissue or skin, a fractured bone, a tumorous tissue or organ, a deformed bone, or a swelling or lump.

At 408, a touch input may be transmitted. The circuitry 202 may be configured to transmit the touch input to the wearable sensor 108 in contact with the first anatomical portion 118 of the body. In some embodiments, the wearable sensor 108 may not be in contact with the first anatomical portion 118 of the body. As shown in a view 408A, the touch input may include the selection of the first region 122 of the first 3D model 120. The touch input may be transmitted to the wearable sensor 108 to initiate acquisition of bio-signals, such as physiological signals (such as the heart rate, the blood pressure, an amount of sweat (Galvanic Skin Response)) and somatic sensation information associated with the human subject 116. In some instances, the bio-signals may also include body temperature information associated with the body of the human subject 116. The wearable sensor 108 may acquire the temperature sensing information with or without any direct contact with the body of the human subject 116.

In accordance with an embodiment, the circuitry 202 may be configured to transmit the touch input to the haptic device 110 in contact with at least the first anatomical portion 118 of the body of the human subject 116. The haptic device 110 may receive the transmitted touch input, via the communication network 112. The haptic device 110 may generate a haptic sensation on the first anatomical portion 118 of the body, based on the received touch input. The haptic sensation may include one or more sensations, such as a touch/tactile sensation on skin, a sensation of warmth or cold in touch, or a pressure applied on the skin with a touch. Through the haptic sensations, the haptic device 110 may allow the human subject 116 to sense and feel a touch on the defect portion of the first anatomical portion 118, when the user 114 touches the first region 122 of the first 3D model 120. Thus, the haptic device 110 may provide a touch and feel experience to the human subject 116.

In accordance with another embodiment, the touch input may be transmitted to a robotic arm instead of the haptic device 110. For example, the touch input may be transmitted via the wearable haptic device 106 in the form of a pressure signal (in response to a touch applied by the user 114 on the first region 122). The robotic arm may maneuver in space to emulate the touch applied by the user 114, on the defect portion in the first anatomical portion 118 of the body. The amount of pressure applied by the user 114 may be experienced by the human subject 116 as a touch sensation on the defect portion in the first anatomical portion 118 of the body.

In accordance with another embodiment, instead of having the wearable sensor 108, one or more sensors may be present around the human subject and may not be in contact with the body of the human subject 116. In such an implementation, the acquisition of the bio-signals, such as the physiological signals, body temperature information, and the somatic sensation information associated with the human subject 116 may be done by such sensors. For example, the body temperature of the human subject 116 may be recorded by usage of a thermal scanner. Additionally, or alternatively, electronic nose technology (such as an artificial nose) may be utilized to analyze breath profile of the human subject 116 for detection of volatile organic compounds that may lead to detection of certain diseases, such as lung cancer and Alzheimer's disease. Additionally, or alternatively, vein visualization technology (VVT) may be utilized to analyze locations of peripheral veins in the human subject 116.

At 410, a set of bio-signals may be received. In accordance with an embodiment, the circuitry 202 may be configured to receive the set of bio-signals from the wearable sensor 108, based on the touch input. The set of bio-signals may be associated with the defect portion in the first anatomical portion 118 of the body. For example, the set of bio-signals may be associated with a swelling on the arm of the human subject 116. The set of bio-signals may include physiological signals and somatic sensation information associated with the defect portion. For example, the physiological signals may include the electrocardiogram (ECG) signal, a respiratory rate, skin conductance, muscle current, electromyogram (EMG), or electroencephalography (EEG) of the human subject 116. The physiological signals may be measured by the wearable sensor 108, which may be in contact with the first anatomical portion 118 of the body of the human subject 116. In accordance with an embodiment, the somatic sensation information may include touch sensation information associated with the defect portion, kinesthetic information associated with the defect portion, and haptic perception information associated with the defect portion. For example, the somatic sensation information may include information, such as a touch on the skin, a pressure applied at different locations on the skin due to the touch, and the temperature of the skin at a time the touch is applied. The touch sensation information may include tactile inputs from the skin of the human subject 116. The kinesthetic information may include information related to pain from the muscles, tendons and joints. The sensations from the internal organs of the human subject 116 may include for example, a sense of fullness of stomach or bladder. The haptic perception information may relate to somatosensory perception of patterns on the skin surface (e.g., edges, curvature, and texture) and proprioception of hand position and conformation.

At 412, the haptic feedback may be generated. In accordance with an embodiment, the circuitry 202 may be configured to control the wearable haptic device 106 to generate the haptic feedback based on the received set of bio-signals. The haptic feedback may be generated as the response to the human touch, such as the touch input from the user 114. In an embodiment, the haptic feedback may include kinesthetic and tactile feedback. The kinesthetic feedback may correspond to sensations in at least one of the muscles, joints, tendons, joint angles of the arm, hand, wrist, fingers, and so forth. The tactile feedback may correspond to the sensations in the fingers or on a surface of the skin, for example, the vibration, the touch, and the texture of the skin. In another embodiment, the wearable haptic device 106 may emulate through the haptic feedback, a warmth or coldness associated the defect portion on a portion of user's skin in contact with the wearable haptic device 106. For example, if the user 114 wears a haptic glove on the right hand and touches a swelling region on a 3D model of a human arm, then the haptic feedback may stimulate sensations which may typically be experienced when the swelling is physically touched in course of a physical examination. Such sensations may include tactile and/or kinesthetic sensation, as well as warmth associated with the swelling.

At 414, an input feature may be generated for the machine learning model 204A. In accordance with an embodiment, the circuitry 202 may be configured to generate the input feature for the machine learning model 204A based on the received set of bio-signals, the medical condition information associated with the human subject 116, and the anthropometric features related to the body of the human subject 116. The input features may include, for example, at least one of the body temperature, the blood pressure of the human subject 116, the medical diseases associated with the human subject 116, such as obesity and thyroid, the BMI of the human subject 116, a skin texture around the defect portion, an x-ray of the first anatomical portion 118, and the like.

The machine learning model 204A may be a trained on a training dataset, which may include bio-signals, medical condition information, and anthropometric features of various test subjects. Details of training of the machine learning model 204A are further provides in FIG. 6, for example.

At 416, the machine learning model 204A may output a recommendation. In accordance with an embodiment, the circuitry 202 may input the generated input feature to the machine learning model 204A and the machine learning model 204A may output the recommendation based on the input feature. In an embodiment, the input to the machine learning model 204A may include datapoints from the received set of bio-signals, the medical condition information, and the anthropometric features in a concatenated form (i.e. the input feature). In another embodiment, the machine learning model 204A may be a hybrid model and may receive datapoints from the received set of bio-signals, the medical condition information, and the anthropometric features at different stages of the machine learning model 204A. Each of such stages may output an inference, which may be later on used to output the recommendation. In an embodiment, the first head-mounted display 104 may render the output recommendation to assist the user 114 (who may be a medical practitioner) to provide a remote consultation to the human subject 116. Examples of the output recommendation may include, but are not limited to, a course of treatment for the defect portion, a current condition of the defect portion, a prognosis for the defect portion, a diagnosis related to the defect portion, or a combination thereof.

In an exemplary scenario, the recommendation may include a set of tests that may be required for the treatment of the human subject 116, such as MRI, X-ray or blood tests. The recommendation may also include categorization of the measured one or more parameters (in the form of bio-signals) by the wearable sensor 108 as a normal statistic, an abnormal statistic, or a highly risky statistic. For example, if the blood pressure measured by the wearable sensor 108 is (140, 80) mmHg, then the output recommendation may categorize the blood pressure as an abnormal statistic. Such categorization may assist the user 114 to prescribe suitable medicines or checkups based on the recommendation. Further, the recommendation may include a suggestive course of treatment for the human subject 116, based on the measured one or more parameters. For example, the recommendation may include details of certain medicines as a suitable prescription for the human subject 116. The recommendation may specify a duration of the treatment of the human subject 116, a current stage of disease (for example, a second stage of leukemia), or an incubation period in case the human subject is diagnosed with a viral or bacterial infection.

In accordance with an embodiment, the circuitry 202 may be configured to extract the recommendation from the machine learning model 204A and control the first head-mounted display 104 to render the recommendation. The recommendation may be rendered by the first head-mounted display 104 in the form of a report to present to the user 114. The recommendation-based report may be analyzed by the user 114 for the treatment of the human subject 116.

At 418, it may be determined whether the recommendation is selected by the user 114. In an embodiment, the circuitry 202 may be configured to determine whether or not the recommendation is selected based on a user input by the user 114. For example, through a user input, the user 114 (who may be a medical practitioner) may approve the recommendation as suitable for the human subject 116. In case the recommendation is selected by the user 114, control may pass to 420. Otherwise, control may pass to 422.

At 420, the selected recommendation may be shared on a display device (such as an eXtended Reality (XR) headset) associated with the human subject 116. In an embodiment, the circuitry 202 may share the selected recommendation on the display device associated with the human subject 116.

At 422, a rescan may be executed. In an embodiment, the circuitry 202 may skip the recommendation (output at 416) and may pass the control to 402. Alternatively, the control may pass to 404 and a 3D model of an anatomical portion of another human subject may be rendered on the first head-mounted display 104. As the control passes to 402 or 404, the user 114 (who may be a medical practitioner) may seamlessly switch between multiple remote consultation (and/or training) sessions with one or more human subjects.

Although the diagram 400 is illustrated as discrete operations, such as 402, 404, 406, 408, 410, 412, 414 416, 418, 420, and 422, however, in certain embodiments, such discrete operations may be further divided into additional operations, combined into fewer operations, or eliminated, depending on the particular implementation without detracting from the essence of the disclosed embodiments.

Figure 5:
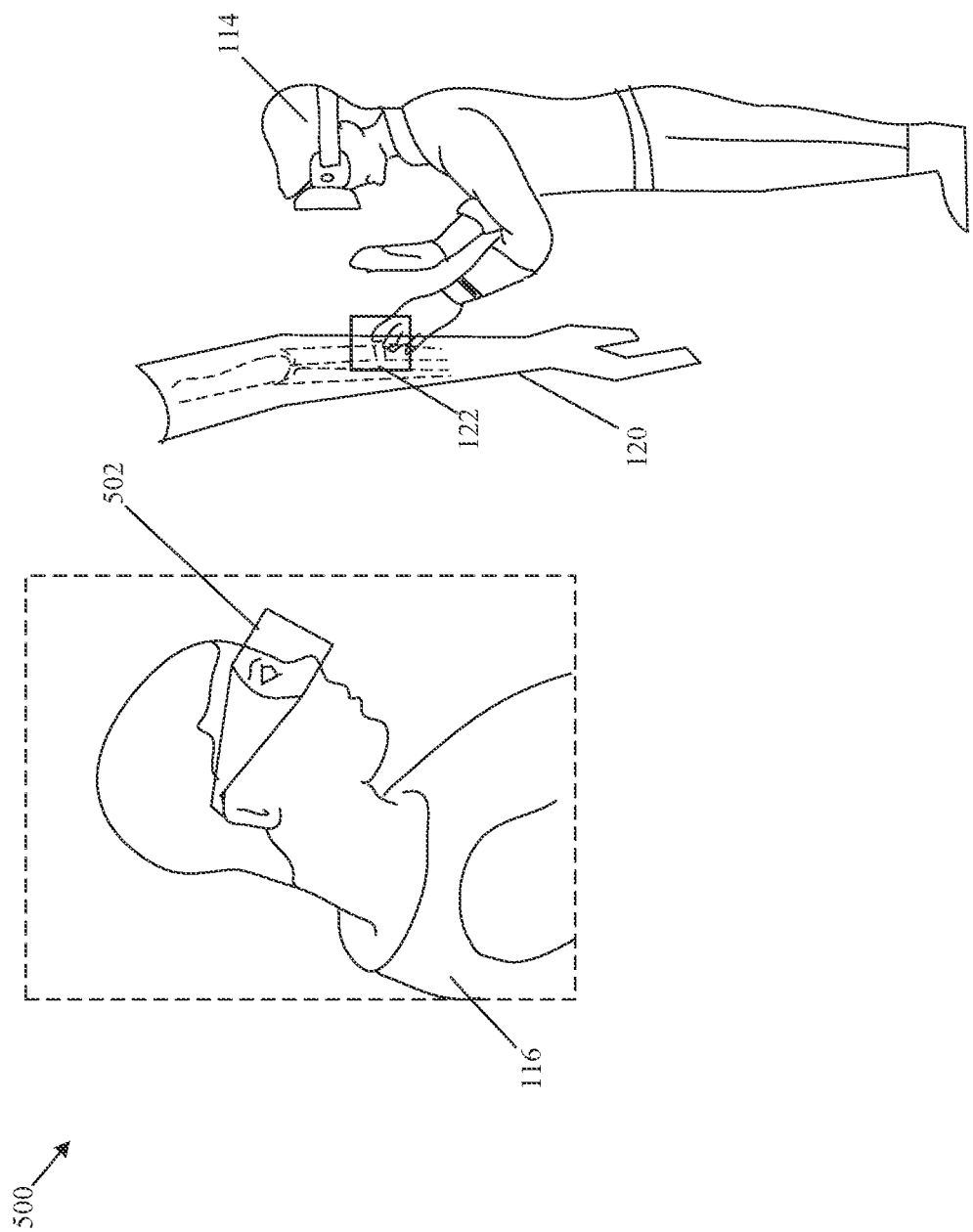
FIG. 5 is a diagram that illustrates an exemplary scenario for usage of a second head-mounted display by a human subject, in accordance with an embodiment of the disclosure.

FIG. 5 is a diagram that illustrates an exemplary scenario for usage of a second head-mounted display by a human subject, in accordance with an embodiment of the disclosure. FIG. 5 is described in conjunction with elements from FIGS. 1, 2, 3 and 4. With reference to FIG. 5, there is shown a scenario 500. The scenario 500 may include the human subject 116 as a wearer of a second head-mounted display 502. The scenario 500 may further include the first 3D model 120 and a second 3D model 504 of at least a human hand of the user 114 while wearing the wearable haptic device 106.

In accordance with an embodiment, the circuitry 202 may be configured to control the second head-mounted display 502 to render the first 3D model 120 and the second 3D model 504. The second head-mounted display 502 may be controlled based on the touch input on the first region 122 of the first 3D model 120. The second 3D model 504 may include at least the human hand of the user 114 and may be rendered to emulate a movement of the human hand while the human hand applies a human touch on the first region 122 of the first 3D model 120.

In an exemplary scenario, the human subject 116 may be present at a location which may be different than a location of the user 114 that may be examining the first 3D model 120 associated with the human subject 116. While the user 114 may be conducting the medical examination, the second head-mounted display 502 may enable the human subject 116 to view what the user 114 may be viewing through the first head-mounted display 104, as well as the hand-movement (i.e. through the second 3D model 504) of the user 114 in real-time or near real-time. In addition, the wearable sensor 108, the wearable haptic device 106, and the haptic device 110 may be utilized to emulate a touch and feel-based experience of a physical medical examination in a virtual remote consultation setup for both the user 114 and the human subject 116.

Figure 6:
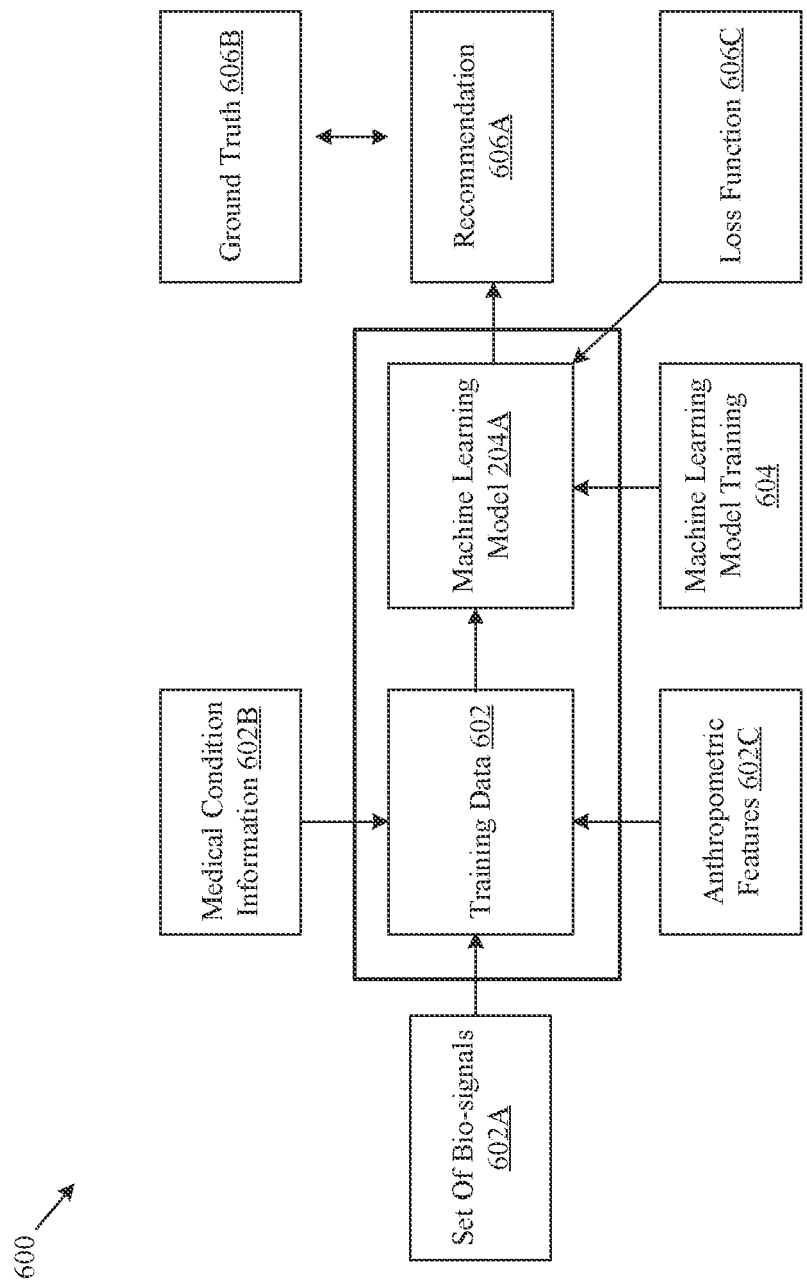
FIG. 6 is a diagram that illustrates exemplary operations for training of a machine learning model, in accordance with an embodiment of the disclosure.

FIG. 6 is a diagram that illustrates exemplary operations for training of a machine learning model, in accordance with an embodiment of the disclosure. FIG. 6 is explained in conjunction with elements from FIGS. 1, 2, 3, 4, and 5. With reference to FIG. 6, there is shown a diagram 600 to depict exemplary operations from 602 to 604. The exemplary operations illustrated in the diagram 600 may start at 602 and may be performed by any computing system, apparatus, or device, such as by the electronic apparatus 102 of FIG. 2.

At 602, training data may be input to the machine learning model 204A. The training data may be multimodal data and may be used to train the machine learning model 204A. The training data may include, for example, a set of bio-signals 602A, medical condition information 602B, and anthropometric features 602C from various test subjects. For example, the training data may be associated with a plurality of human test subjects who have been medically examined in the past.

Several input features may be generated for the machine learning model 204A based on the training data (which may be obtained from a medical record database). The training data may include a variety of datapoints associated with health disorders, diseases, injuries, lab tests, medical imagery, and other related information. For example, the training data may include datapoints related to a human subject with more than one disease or medical condition, such as diabetes and hypertension. Additionally, or alternatively, the training data may include datapoints related to human subjects with different kinds of health diseases and disorders, such as lifestyle-based diseases (such as obesity) and genetic disorders (such as Down's syndrome). The training data may further include datapoints related to human subjects with varying age, gender, and anthropometric features, such as a BMI, a height, or a weight of each of such subjects.

At 604, the machine learning model 204A may be trained on the training data. Before training, a set of hyperparameters may be selected based on a user input, for example, from a software developer. For example, a specific weight may be selected for each datapoint in the input feature generated from the training data.

In training, several input features may be sequentially passed as inputs to the machine learning model 204A. The machine learning model 204A may output several recommendations (such as a recommendation 606A) based on such inputs. Each of such recommendations may be compared with a ground truth recommendation (such as a ground truth 606B). Parameters, such as weights of the machine learning model 204A may be updated based on an optimization algorithm (such as stochastic gradient descent) to minimize a loss function 606C for the machine learning model 204A. The value of the loss function 606C for a given pair of input feature and output recommendation may determine an extent by which the output recommendation deviates from the ground truth recommendation. In an embodiment, a training error may be computed based on the loss function 606C. The loss function 606C may be used to determine an error in the prediction by the machine learning model 204A. For example, the loss function 606C may indicate a loss value (i.e. above a threshold, such as 50%) if the recommendation 606A is incorrect (when compared to the ground truth 606A).

Once trained, the machine learning model 204A may select higher weights for datapoints in the input feature which may contribute more to the output recommendation than other datapoints in the input feature. As an example, if the input feature is generated for identification of a fracture on the left knee of a test subject, a higher weight may be given to a skin color and a degree of swelling around the left knee than the body temperature of the test subject.

In an exemplary scenario, the input feature may include symptoms associated with a human subject, such as "high fever, cough and cold". The machine learning model 204A may output a recommendation as "prescribe fever medicines and antibiotics". If the ground truth 606A also includes a recommendation of treatment as "prescribe fever medicines and antibiotics", then the output of the machine learning model 204A may be considered as accurate and ready for deployment. In some cases, the recommendation output by the machine learning model 204A may be validated by the user 114, such as the medical practitioner. For example, the recommendation output may be categorized as a "successful recommendation", a "partially successful recommendation" or a "failed recommendation" by the user 114 based on the accuracy of the recommendations.

Although the diagram 600 is illustrated as discrete operations, such as 602, 604 and 606, however, in certain embodiments, such discrete operations may be further divided into additional operations, combined into fewer operations, or eliminated, depending on the particular implementation without detracting from the essence of the disclosed embodiments.

Figure 7:
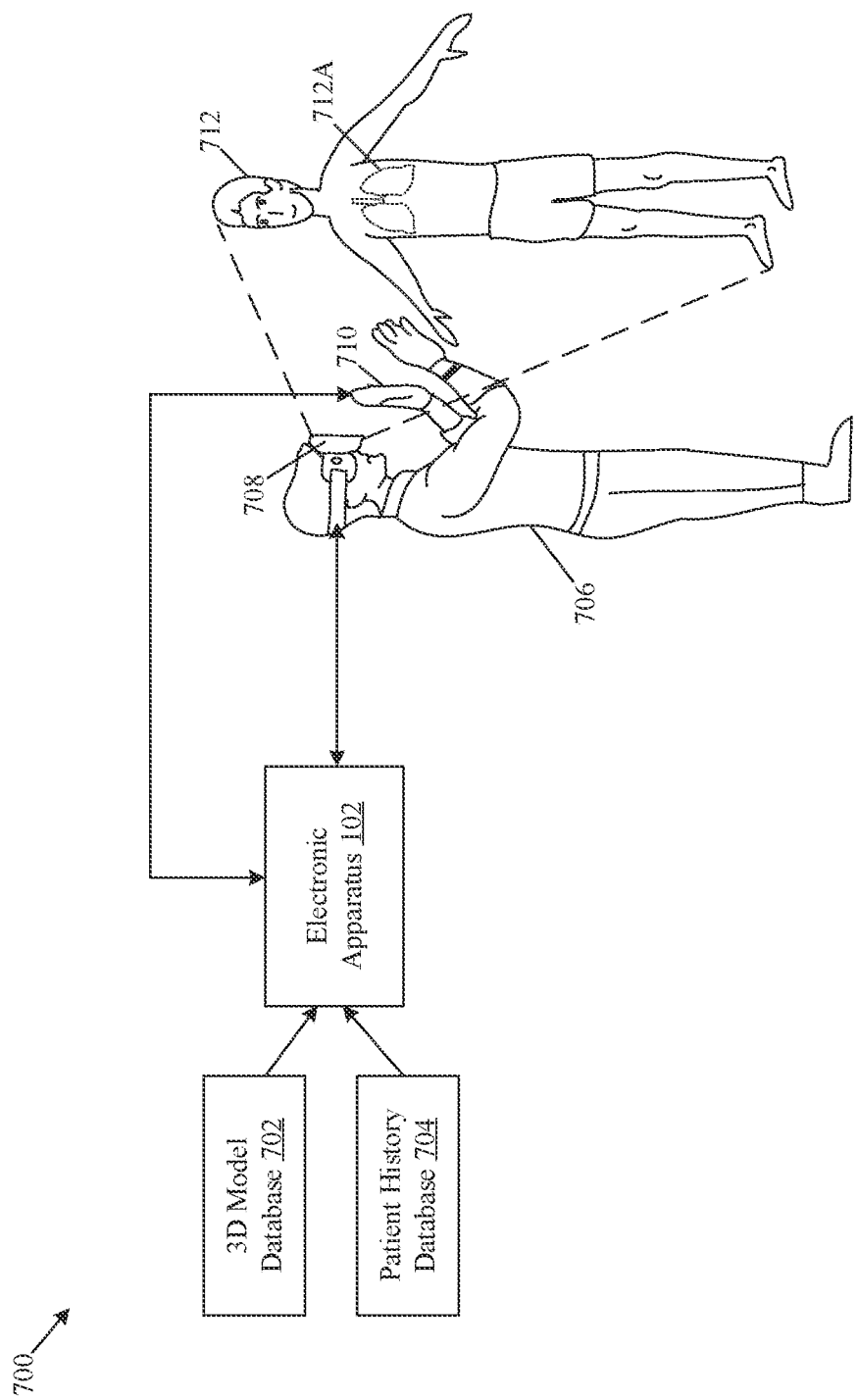
FIG. 7 is a diagram that illustrates an exemplary scenario for utilization of a 3D model from a 3D model database for training a user, in accordance with an embodiment of the disclosure.

FIG. 7 is a diagram that illustrates an exemplary scenario for utilization of a 3D model from a 3D model database for training a user, in accordance with an embodiment of the disclosure. FIG. 7 is described in conjunction with elements from FIGS. 1, 2, 3, 4, 5, and 6. With reference to FIG. 7, there is shown a scenario 700. In the scenario 700, there is shown a 3D model database 702, a patient history database 704, and a user 706, a head-mounted device 708, a wearable haptic device 710, a 3D model 712, and a first region corresponding to an internal organ 712A in the 3D model 712.

The electronic apparatus 102 may be configured to control the head-mounted device 708 to render the 3D model 712 for a purpose of training of the user 706, who may be a medical student or trainee in medicine. As an example, the 3D model 712 may be rendered in the form of VR object(s). The electronic apparatus 102 may receive the 3D model 712 from the 3D model database 702 (associated with one or more hospitals). Furthermore, the electronic apparatus 102 may access the patient history database 704 that may include a first set of features (as described in FIG. 4) and a second set of features (as described in FIG. 4) associated with a test subject.

For the training purpose, the electronic apparatus 102 may render a defect portion (e.g., a bruise or a fracture) based on information accessed from the patient history database 704. At any time-instant, the user 706 may touch any location on the 3D model 712. In response, the electronic apparatus 102 may receive a touch input and may extract from the patient history database 704, a set of bio-signals. Such bio-signals may have been acquired in the past or may be synthetically generated based on a mathematical model of touch sensation. The electronic apparatus 102 may control the wearable haptic device 710 (worn by the user 706) to generate a haptic feedback based on the set of bio-signals. For the user 706, the haptic feedback may stimulate sensations which may be typically experienced when a defect portion (such as a fractured knee) is touched at the time of a physical examination.

In one embodiment, the 3D model 712 may further include the first region corresponding to the internal organ 712A (such as lungs) of the patient. The patient history database 704 may include medical records of a plurality of patients with various types of health diseases and disorders (such as multiple defect combinations). For example, the 3D model 712 associated with a human subject may be generated based on a bone fracture in an arm of the human subject and a cancer of a specific organ (such as the internal organ 712A) of the human subject. The electronic apparatus 102 may activate options (such as user-interface (UI) elements or touch gestures on the head-mounted device 708 to allow a user to select and view different regions of the 3D model 712 and different datapoints (included in the patient history database 704) related to the 3D model 712.

Figure 8:
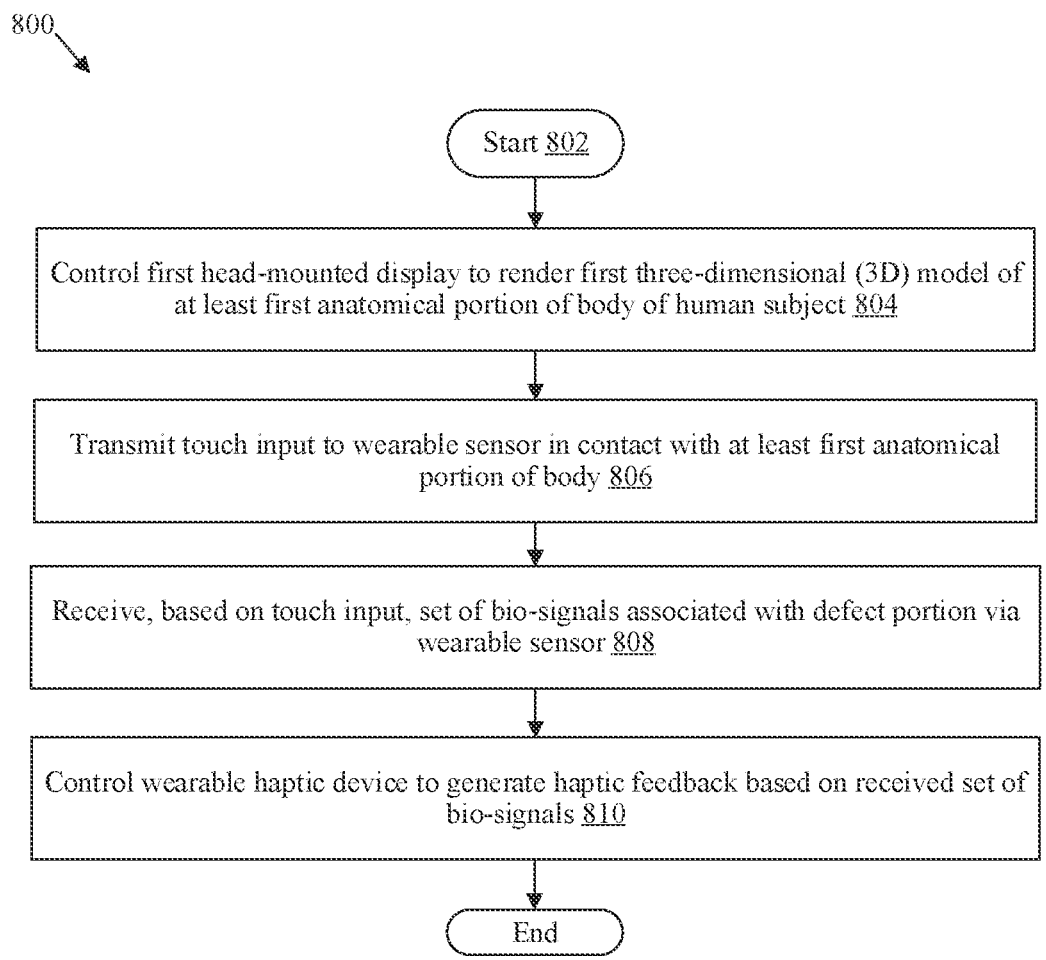
FIG. 8 is a flowchart that illustrates an exemplary method for medical examination of human body using haptics, in accordance with an embodiment of the disclosure.

FIG. 8 is a flowchart that illustrates an exemplary method for medical examination of human body using haptics, in accordance with an embodiment of the disclosure. FIG. 8 is described in conjunction with elements from FIGS. 1, 2, 3, 4, 5, 6, and 7. With reference to FIG. 8, there is shown a flowchart 800. The exemplary method of the flowchart 800 may be executed by any computing system, for example, by the electronic apparatus 102 of FIG. 1. The exemplary method of the flowchart 800 may start at 802 and proceed to 804.

At 804, the first head-mounted display 104 may be controlled to render the first 3D model 120 of at least the first anatomical portion 118 of the body of the human subject 116. In accordance with an embodiment, the circuitry 202 may be configured to control the first head-mounted display 104 to render the first 3D model 120 of at least the first anatomical portion 118 of the body of the human subject 116. The rendered first 3D model 120 may include the first region 122 corresponding to the defect portion in the first anatomical portion 116 of the body of the human subject 116.

At 806, a touch input may be transmitted to the wearable sensor 108 in contact with at least the first anatomical portion 118 of the body. In accordance with an embodiment, the circuitry 202 may be configured to transmit the touch input to the wearable sensor 108 in contact with at least the first anatomical portion 118 of the body of the human subject 116. The transmitted touch input may correspond to the human touch on the first region 122 of the rendered first 3D model 120.

At 808, a set of bio-signals associated with the defect portion may be received via the wearable sensor 108, based on the touch input. In accordance with an embodiment, the circuitry 202 may be configured to receive the set of bio-signals associated with the defect portion via the wearable sensor 108. The set of bio-signals may include the physiological signals and the somatic sensation information associated with the defect portion, as described in FIG. 4, for example.

At 810, the wearable haptic device 106 may be controlled to generate the haptic feedback based on the received set of bio-signals. In accordance with an embodiment, the circuitry 202 may be configured to control the wearable haptic device 106 to generate the haptic feedback based on the received set of bio-signals. The haptic feedback may be generated as the response to the human touch.

Although the flowchart 800 illustrates discrete operations, such as 804, 806, 808, and 810 the disclosure is not so limited. Accordingly, in certain embodiments, such discrete operations may be further divided into additional operations, combined into fewer operations, or eliminated, depending on the particular implementation without detracting from the essence of the disclosed embodiments.

Various embodiments of the disclosure may provide a non-transitory computer-readable medium and/or storage medium having stored thereon, computer-executable instructions executable by a machine and/or a computer (for example the electronic apparatus 102). The instructions may cause the machine and/or computer (for example the electronic apparatus 102) to perform operations that include control of the first head-mounted display 104 to render the first three-dimensional (3D) model 120 of at least the first anatomical portion 118 of the body of the human subject 116. The rendered first 3D model 120 may include the first region 122 corresponding to the defect portion in the first anatomical portion 118 of the body. The operations may further include transmission of the touch input to the wearable sensor 108 in contact with at least the first anatomical portion 118 of the body. The transmitted touch input may correspond to the human touch on the first region 122 of the rendered first 3D model 120. The operations may further include reception, based on the touch input, of the set of bio-signals associated with the defect portion via the wearable sensor 108. The set of bio-signals may include physiological signals and somatic sensation information associated with the defect portion. Furthermore, the operations may include control of the wearable haptic device 106 to generate the haptic feedback based on the received set of bio-signals. The haptic feedback may be generated as a response to the human touch.

Exemplary aspects of the disclosure may include an electronic apparatus (such as the electronic apparatus 102) that may include circuitry (such as the circuitry 202) communicatively coupled to a first head-mounted display (such as the first head-mounted display 104) and a wearable haptic device (such as the wearable haptic device 106). The circuitry 202 may be configured to control the first head-mounted display 104 to render a first three-dimensional (3D) model (such as the first 3D model 120) of at least a first anatomical portion (such as the first anatomical portion 118) of a body of a human subject (such as the human subject 116). The rendered first 3D model 120 may include a first region (such as the first region 122) corresponding to a defect portion in the first anatomical portion 118 of the body. The circuitry 202 may be further configured to transmit a touch input to a wearable sensor (such as the wearable sensor 108) in contact with at least the first anatomical portion 118 of the body. The transmitted touch input may correspond to a human touch on the first region 122 of the rendered first 3D model 120. The circuitry 202 may be further configured to receive, based on the touch input, a set of bio-signals associated with the defect portion via the wearable sensor 108. The set of bio-signals may include physiological signals and somatic sensation information associated with the defect portion. The circuitry 202 may be further configured to control the wearable haptic device 106 to generate a haptic feedback based on the received set of bio-signals. The haptic feedback may be generated as a response to the human touch.

In accordance with an embodiment, the first region 122 of the first 3D model 120 may correspond to the defect portion, which may be one of a tissue deformation or defect, a bruised tissue or skin, a fractured bone, a tumorous tissue or organ, a deformed bone, or a swelling or lump.

In accordance with an embodiment, the circuitry 202 may be further configured to receive depth information associated with the defect portion from one or more imaging sensors (such as the first imaging sensor 302A, the second imaging sensor 302B and the third imaging sensor 302C). The circuitry 202 may further generate the first region 122 corresponding to the defect portion in the first anatomical portion 118 of the body, based the received depth information.

In accordance with an embodiment, the circuitry 202 may be further configured to control a camera rig comprising one or more imaging sensors (such as the first imaging sensor 302A, the second imaging sensor 302B and the third imaging sensor 302C) to scan at least the first anatomical portion 118 of the body of the human subject 116. The circuitry 202 may further receive 3D scan data of at least the first anatomical portion 118 of the body of the human subject 116 based on the scan. The circuitry 202 may further control the first head-mounted display 104 to render the first 3D model 120 of at least the first anatomical portion 118 of the body based on the received 3D scan data.

In accordance with an embodiment, the 3D scan data may include a 3D representation of at least one internal organ of the human subject 116.

In accordance with an embodiment, the circuitry 202 may be further configured to receive a first set of features (such as the first set of features 404C) that includes anthropometric features related to the body of the human subject 116 and medical condition information associated with the human subject 116. The circuitry 202 may be further configured to generate the first 3D model 120 based on the received first set of features 404C. The generated first 3D model 120 may be rendered on the first head-mounted display 104.

In accordance with an embodiment, the circuitry 202 may be further configured to receive a second set of features (such as the second set of features 404C) related to the defect portion in the first anatomical portion 118 of the body of the human subject 116. The received second set of features 404C may include appearance attributes associated with the defect portion.

In accordance with an embodiment, the circuitry 202 may be further configured to update the generated first 3D model 120 by a mesh deformation of at least the first region 122 of the generated first 3D model 120. The mesh deformation may be applied based on the received second set of features 404C. The updated first 3D model 120 may be rendered on the first head-mounted display 104.

In accordance with an embodiment, the second set of features 404C may include at least one of physical deformities associated with at least the first anatomical portion 118 of the body or deformities associated with one or more internal organs of the body.

In accordance with an embodiment, the somatic sensation information may include touch sensation information associated with the defect portion, kinesthetic information associated with the defect portion, and haptic perception information associated with the defect portion.

In accordance with an embodiment, the circuitry 202 may be further configured to generate an input feature for a machine learning model (such as the machine learning model 204A) based on the received set of bio-signals, medical condition information associated with the human subject 116, and anthropometric features related to the body of the human subject 116. The circuitry 202 may further input the generated input feature to the machine learning model 204A. The machine learning model 204A outputs a recommendation based on the input feature.

In accordance with an embodiment, the recommendation may include at least one of: a course of treatment for the defect portion, a current condition of the defect portion, a prognosis for the defect portion, and a diagnosis related to the defect portion.

In accordance with an embodiment, the circuitry 202 may be further configured to extract the recommendation from the machine learning model 204A. The circuitry 202 may further control the first head-mounted display 104 to render the recommendation.

In accordance with an embodiment, the circuitry 202 may be further configured to transmit the touch input to a haptic device (such as the haptic device 110) in contact with at least the first anatomical portion 118 of the body of the human subject 116. The haptic device 110 may receive the transmitted touch input and generate a haptic sensation on the first anatomical portion 118 of the body, based on the received touch input.

In accordance with an embodiment, the circuitry 202 may be further configured to control a second head-mounted display (such as the second head-mounted display 502), as worn on a head of the human subject 116, to render the first 3D model 120 and a second 3D model comprising a human hand. The second 3D model may be rendered to emulate a movement of the human hand while the human hand applies the human touch on the first region 122 of the rendered 3D first model 120. The second head-mounted display 502 may be controlled based on the received touch input.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that includes a portion of an integrated circuit that also performs other functions.

The present disclosure may also be embedded in a computer program product, which includes all the features that enable the implementation of the methods described herein, and which when loaded in a computer system is able to carry out these methods. Computer program, in the present context, means any expression, in any language, code or notation, of a set of instructions intended to cause a system with information processing capability to perform a particular function either directly, or after either or both of the following: a) conversion to another language, code or notation; b) reproduction in a different material form.

While the present disclosure is described with reference to certain embodiments, it will be understood by those skilled in the art that various changes may be made, and equivalents may be substituted without departure from the scope of the present disclosure. In addition, many modifications may be made to adapt a particular situation or material to the teachings of the present disclosure without departure from its scope. Therefore, it is intended that the present disclosure is not limited to the particular embodiment disclosed, but that the present disclosure will include all embodiments that fall within the scope of the appended claims.

What is claimed is:

1. An electronic apparatus, comprising:
circuitry communicatively coupled to a first head-mounted display and a wearable haptic device in contact with a user, wherein the circuitry is configured to:
control the first head-mounted display to render a first three-dimensional (3D) model of at least a first anatomical portion of a body of a human subject, wherein
the human subject is different from the user, and
the rendered first 3D model comprises a first region corresponding to a defect portion in the first anatomical portion of the body;
transmit a touch input to a wearable sensor in contact with at least the first anatomical portion of the body of the human subject, wherein the transmitted touch input corresponds to a human touch, by the user, on the first region of the rendered first 3D model, and the transmitted touch input includes at least a pressure signal indicating an amount of pressure applied during the human touch by the user;

receive, based on the touch input, a set of bio-signals associated with the defect portion via the wearable sensor, wherein the set of bio-signals comprises physiological signals and somatic sensation information associated with the defect portion;

control the wearable haptic device to generate a haptic feedback based on the received set of bio-signals, wherein the haptic feedback is generated as a response to the human touch;

receive a first set of features comprising anthropometric features related to the body of the human subject and medical condition information associated with the human subject;

generate an input feature for a machine learning model based on the received set of bio-signals, the anthropometric features related to the body of the human subject, and the medical condition information associated with the human subject; and input the generated input feature to the machine learning model, wherein the machine learning model outputs a recommendation based on the input feature.

2. The electronic apparatus according to claim 1, wherein the first region of the first 3D model corresponds to the defect portion, which is one of a tissue deformation or defect, a bruised tissue or skin, a fractured bone, a tumorous tissue or organ, a deformed bone, or a swelling or lump.

3. The electronic apparatus according to claim 1, wherein the circuitry is further configured to:

receive depth information associated with the defect portion from one or more imaging sensors; and generate the first region corresponding to the defect portion in the first anatomical portion of the body, based the received depth information.

4. The electronic apparatus according to claim 1, wherein the circuitry is further configured to:

control a camera rig comprising one or more imaging sensors to scan at least the first anatomical portion of the body of the human subject;

receive 3D scan data of at least the first anatomical portion of the body of the human subject based on the scan; and control the first head-mounted display to render the first 3D model of at least the first anatomical portion of the body based on the received 3D scan data.

5. The electronic apparatus according to claim 4, wherein the 3D scan data comprises a 3D representation of at least one internal organ of the human subject.

6. The electronic apparatus according to claim 1, wherein the circuitry is further configured to generate the first 3D model based on the received first set of features, and the generated first 3D model is rendered on the first head-mounted display.

7. The electronic apparatus according to claim 6, wherein the circuitry is further configured to update the generated first 3D model by a mesh deformation of at least the first region of the generated first 3D model, the mesh deformation is applied based on the received second set of features, and the updated first 3D model is rendered on the first head-mounted display.

8. The electronic apparatus according to claim 1, wherein the circuitry is further configured to receive a second set of features related to the defect portion in the first anatomical portion of the body of the human subject, and the received second set of features comprises appearance attributes associated with the defect portion.

9. The electronic apparatus according to claim 8, wherein the second set of features comprises at least one of physical deformities associated with at least the first anatomical portion of the body or deformities associated with one or more internal organs of the body.

10. The electronic apparatus according to claim 1, wherein the somatic sensation information comprises touch sensation information associated with the defect portion, kinesthetic information associated with the defect portion, and haptic perception information associated with the defect portion.

11. The electronic apparatus according to claim 1, wherein the recommendation comprises at least one of a course of treatment for the defect portion, a current condition of the defect portion, a prognosis for the defect portion, and a diagnosis related to the defect portion.

12. The electronic apparatus according to claim 1, wherein the circuitry is further configured to:

extract the recommendation from the machine learning model; and control the first head-mounted display to render the recommendation.

13. The electronic apparatus according to claim 1, wherein the circuitry is further configured to transmit the touch input to a haptic device in contact with at least the first anatomical portion of the body of the human subject, and the haptic device:

receives the transmitted touch input; and generates a haptic sensation on the first anatomical portion of the body, based on the received touch input.

14. The electronic apparatus according to claim 1, wherein the circuitry is further configured to control a second head-mounted display, as worn on a head of the human subject, to render the first 3D model and a second 3D model comprising a human hand, the second 3D model is rendered to emulate a movement of the human hand while the human hand applies the human touch on the first region of the rendered 3D first model, and the second head-mounted display is controlled based on the received touch input.

15. A method, comprising:

controlling a first head-mounted display to render a first three-dimensional (3D) model of at least a first anatomical portion of a body of a human subject, wherein the rendered first 3D model comprises a first region corresponding to a defect portion in the first anatomical portion of the body;

transmitting a touch input to a wearable sensor in contact with at least the first anatomical portion of the body of the human subject, wherein the transmitted touch input corresponds to a human touch, by a user, on the first region of the rendered first 3D model, the human subject is different from the user, and the transmitted touch input includes at least a pressure signal indicating an amount of pressure applied during the human touch by the user;

receiving, based on the touch input, a set of bio-signals associated with the defect portion via the wearable sensor, wherein the set of bio-signals comprises physiological signals and somatic sensation information associated with the defect portion;

controlling a wearable haptic device, in contact with the user, to generate a haptic feedback based on the received set of bio-signals, wherein the haptic feedback is generated as a response to the human touch;

receiving a first set of features comprising anthropometric features related to the body of the human subject and medical condition information associated with the human subject;

generating an input feature for a machine learning model based on the received set of bio-signals, the anthropometric features related to the body of the human subject, and the medical condition information associated with the human subject; and inputting the generated input feature to the machine learning model, wherein the machine learning model outputs a recommendation based on the input feature.

16. The method according to claim 15, further comprising:

extracting the recommendation from the machine learning model; and controlling the first head-mounted display to render the recommendation.

17. The method according to claim 15, further comprising:

transmitting the touch input to a haptic device in contact with at least the first anatomical portion of the body of the human subject;

receiving, by the haptic device, the transmitted touch input; and generating, by the haptic device, a haptic sensation on the first anatomical portion of the body, based on the received touch input.

18. A non-transitory computer-readable medium having stored thereon, computer-executable instructions that when executed by an electronic apparatus, causes the electronic apparatus to execute operations, the operations comprising:

controlling a first head-mounted display to render a first three-dimensional (3D) model of at least a first anatomical portion of a body of a human subject, wherein the rendered first 3D model comprises a first region corresponding to a defect portion in the first anatomical portion of the body;

transmitting a touch input to a wearable sensor in contact with at least the first anatomical portion of the body of the human subject, wherein the transmitted touch input corresponds to a human touch, by a user, on the first region of the rendered first 3D model, the human subject is different from the user, and the transmitted touch input includes at least a pressure signal indicating an amount of pressure applied during the human touch by the user;

receiving, based on the touch input, a set of bio-signals associated with the defect portion via the wearable sensor, wherein the set of bio-signals comprises physiological signals and somatic sensation information associated with the defect portion;

controlling a wearable haptic device, in contact with the user, to generate a haptic feedback based on the received set of bio-signals, wherein the haptic feedback is generated as a response to the human touch;

receiving a first set of features comprising anthropometric features related to the body of the human subject and medical condition information associated with the human subject;

generating an input feature for a machine learning model based on the received set of bio-signals, the anthropometric features related to the body of the human subject, and the medical condition information associated with the human subject; and inputting the generated input feature to the machine learning model, wherein the machine learning model outputs a recommendation based on the input feature.

19. The electronic apparatus according to claim 1, wherein the wearable sensor measures at least one parameter associated with the human subject, based on the touch input transmitted to the wearable sensor.

* * * * *